United States Patent [19]

Ávár

[11] Patent Number: 4,730,017

[45] Date of Patent: Mar. 8, 1988

[54] 2,2,6,6-TETRAALKYL-PIPERIDINE COMPOUNDS USEFUL AS LIGHT STABILIZERS

[75] Inventor: Lajos Ávár, Biel-Benken, Switzerland

[73] Assignee: Sandoz Ltd., Basle, Switzerland

[21] Appl. No.: 907,359

[22] Filed: Sep. 12, 1986

[30] Foreign Application Priority Data

Sep. 13, 1985 [GB] United Kingdom ............... 8522666
Dec. 4, 1985 [DE] Fed. Rep. of Germany ....... 3542858
Feb. 5, 1986 [GB] United Kingdom ............... 8602834

[51] Int. Cl.⁴ ..................... C07D 401/12; C08K 5/34
[52] U.S. Cl. ........................... 524/103; 524/99; 524/102; 546/16; 546/190; 546/245; 546/247
[58] Field of Search ............... 546/16, 190, 245, 247; 524/99, 102, 103

[56] References Cited

FOREIGN PATENT DOCUMENTS 582250  7/1976  U.S.S.R. ........................ 546/190

Primary Examiner—Robert T. Bond
Attorney, Agent, or Firm—Gerald D. Sharkin; Richard E. Vila; Thomas C. Doyle

[57] ABSTRACT

A compound useful as a light-stabilizer for polymeric material of formula I

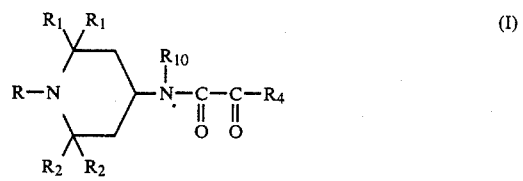

in which R is hydrogen, oxygen, $C_{1-8}$alkyl or —CO—$R_5$, where $R_5$ is —C($R_{10}$)=$CH_2$, $C_{1-6}$alkyl, phenyl, —CO—O—$C_{1-4}$alkyl or —N$R_7R_8$ and where $R_7$ is hydrogen, $C_{1-12}$alkyl, $C_{5-6}$-cycloalkyl, phenyl, phenyl$C_{1-4}$alkyl or $C_{1-12}$alkylphenyl and $R_8$ is $C_{1-12}$alkyl or hydrogen;

each $R_1$, independently, is —$CH_3$ or —$CH_2(C_{1-4}$alkyl) or both groups $R_1$ form a group —$(CH_2)_5$—;

each $R_2$, independently, is —$CH_3$ or —$CH_2(C_{1-4}$alkyl) or both groups $R_2$ form a group —$(CH_2)_5$);

$R_{10}$ is hydrogen or $C_{1-4}$alkyl; and $R_4$ is an amide- or ester-forming group.

27 Claims, No Drawings

4,730,017

2,2,6,6-TETRAALKYL-PIPERIDINE COMPOUNDS USEFUL AS LIGHT STABILIZERS

The invention relates to novel tetraalkylpiperidine products useful as light stabilisers for polymeric systems.

According to the invention there is provided a compound of formula I

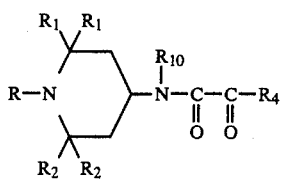

in which R is hydrogen, oxygen, $C_{1-8}$alkyl or —CO—$R_5$, where $R_5$ is —C($R_{10}$)=$CH_2$, $C_{1-6}$alkyl, phenyl, —CO—O—$C_{1-4}$alkyl or —$NR_7R_8$ and where $R_7$ is hydrogen, $C_{1-12}$alkyl, $C_{5-6}$cycloalkyl, phenyl, phenyl$C_{1-4}$alkyl or $C_{1-12}$alkylphenyl and $R_8$ is $C_{1-12}$alkyl or hydrogen;

each $R_1$, independently, is —$CH_3$ or —$CH_2$($C_{1-4}$alkyl) or both groups $R_1$ form a group —$(CH_2)_5$—;
each $R_2$, independently, is —$CH_3$ or —$CH_2$($C_{1-4}$alkyl) or both groups $R_2$ form a group —$(CH_2)_5$—;
$R_{10}$ is hydrogen or $C_{1-4}$alkyl; and
$R_4$ is an amide- or ester-forming group with the proviso that when R is hydrogen, then $R_4$ is not (i) N unsubstituted 2,2,6,6-tetraalkylpiperidine 4-amino; or
(ii) unsubstituted phenylamino.

Preferably each group $R_1$ is methyl and preferably each group $R_2$ is methyl.

Amide forming groups are preferably those of the formula

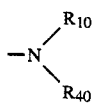

where $R_{10}$ is hydrogen or $C_{1-4}$alkyl and $R_{40}$ is an aliphatic, cycloaliphatic, aromatic or heterocyclic (non-aromatic or aromatic) group, all of which may bear substituents (preferably 1 to 3) selected from $C_{1-4}$alkoxy, $C_{1-4}$alkoxy-$C_{1-12}$alkyl, $C_{1-4}$alkoxy $C_{1-4}$alkoxy, $C_{1-12}$alkyl-mercapto, $C_{1-12}$alkylamino, $C_{1-12}$alkylamino-$C_{1-12}$alkylamino, phenoxy, phenyl-mercapto, phenylamino, acryloyloxy, methacryloyloxy, and tetraalkylpiperidine groups, or by oxalamido or acyloxy groups which may be further substituted by tetraalkylpiperidine groups. The aliphatic groups may also be substituted by substituents selected from hydroxy and phenyl (optionally further substituted). The aliphatic groups are linear or branched and (without any substitution) preferably contain 1 to 22 carbon atoms, more preferably 2 to 12.

Ester forming groups include groups of the formula —$OR_{40}$ where $R_{40}$ is as defined above.

Preferred aliphatic groups as $R_{40}$ are unsubstituted or substituted $C_{1-12}$alkyl groups uninterrupted or interrupted by 1 or 2 groups selected from —O— and —NH—.

Preferred cycloaliphatic groups are unsubstituted or mono-, di- or tri-substituted $C_{5-6}$cycloalkyl, preferably cyclohexyl.

Preferred heterocyclic groups are N-unsubstituted or N-alkyl or N-acyl substituted 2,2,6,6-tetraalkyl piperidine groups.

Preferred aromatic groups are phenyl unsubstituted or mono- or di-substituted by halogen, $C_{1-4}$alkyl or $C_{1-4}$alkoxy.

Preferred substituents of the substituted alkyl groups are selected from —$(X)_y R_9$ (defined below), —OH,

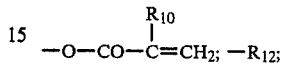

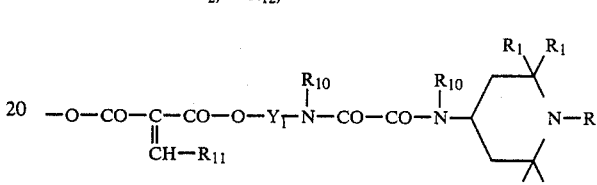

or

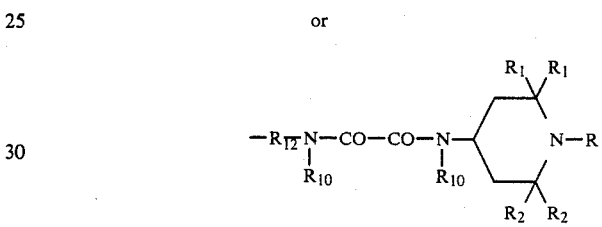

where $Y_1$, $R_{11}$ and $R_{12}$ are defined below
and R, $R_1$, $R_2$ and $R_{10}$ are as defined above.

Where any symbol appears more than once in a formula its significances are independent of one another. Preferably any $C_{1-4}$alkyl in this specification is methyl, and any $C_{1-4}$alkoxy group is preferably methoxy or ethoxy, more preferably methoxy.

In this specification any phenyl or $C_{5-6}$cycloalkyl present is unsubstituted or substituted by 1 to 3 substituents selected from $C_{1-4}$alkoxy, halogen, $C_{1-6}$alkyl or —OH, provided only one substituent may be —OH. Preferably $C_{5-6}$cycloalkyl is cyclohexyl.

Preferred compounds of formula I are those of any one of formulae II to V defined below

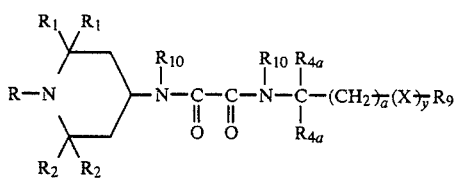

in which
R, $R_1$, $R_2$ and $R_{10}$ are as defined above
X is —O—, —NH— or —S—;
y is 0 or 1;
a is 0 or 1;
each
$R_{4a}$, independently, is hydrogen, $CH_2OH$ or $C_{1-4}$alkyl; and
$R_9$ is linear or branched $C_{1-6}$alkyl unsubstituted or mono- or di-substituted by OH;

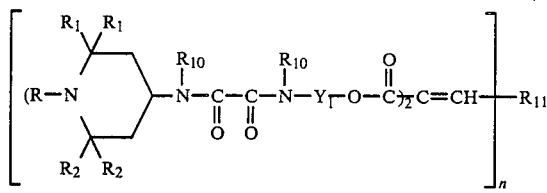
(III)

in which
R, $R_1$, $R_2$ and $R_{10}$ are as defined above;
n is 1 or 2 (preferably 1);
$Y_1$ is linear or branched unsubstituted $C_{1-8}$alkylene, uninterrupted or interrupted by 1 or 2 groups selected from —O— and —NH—;
and $R_{11}$ is an aromatic group unsubstituted or substituted by one or two groups selected from $C_{1-4}$alkyl, $C_{1-4}$alkoxy, and not more than one —OH;

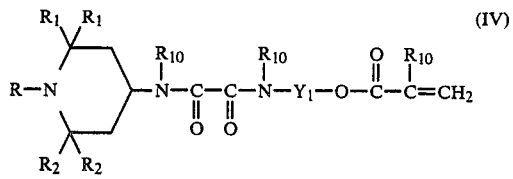
(IV)

in which
R, $R_1$, $R_2$, $R_{10}$ and $Y_1$ are as defined above;

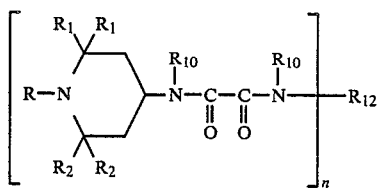
(V)

in which
R, $R_1$, $R_2$ and $R_{10}$ are as defined above;
n is 1 or 2;
$R_{12}$, when monovalent (n=1), is linear or branched $C_{8-22}$alkyl or a group of formula (a) or (b)

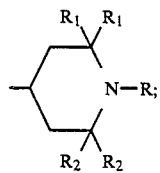
(a)

or

(b)

where
$R_{13}$ is $C_{1-4}$alkyl or $C_{1-4}$alkoxy, or hydrogen;
with the proviso that,
when $R_{12}$ is a group of formula (a), at least one group R is other than hydrogen and
when R is hydrogen and $R_{12}$ is a group of formula (b), $R_{13}$ is not hydrogen;

and $R_{12}$, when divalent (n=2), is linear or branched $C_{1-12}$alkylene or $C_{2-12}$alkenylene.

There is provided according to a further aspect of the invention a compound of formula VI

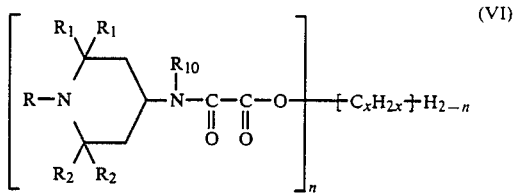
(VI)

in which n is 1 or 2, x is an integer from 1 to 22 inclusive and the other symbols are as defined above.
Preferably $R_9$ is $R_9'$ where $R_9'$ is —$CH_2$—OH; —$(CH_2)_2OH$; —CH(OH)$CH_3$; —C(CH$_3$)$_2$—CH$_2$OH; —CH$_2$—CH(OH)—CH$_3$; —CH$_2$C(CH$_3$)$_2$CH$_2$OH or —CH(CH$_2$CH$_3$)—CH$_2$OH.

Preferred compounds of formula II are of formula IIa

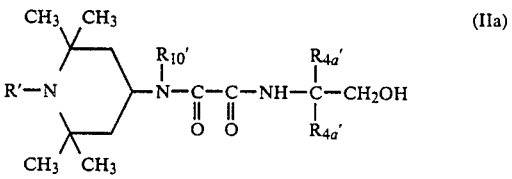
(IIa)

in which
R' is hydrogen, $C_{1-4}$alkyl, —CO—$R_5'$ or —CO—CH=CH$_2$ where $R_5'$ is $C_{1-4}$alkyl or —CO—O—$C_{1-4}$alkyl;
each $R_{4a}'$ independently, is hydrogen or methyl and
$R_{10}'$ is hydrogen or methyl.

Preferred compounds of formula III are of formula IIIa

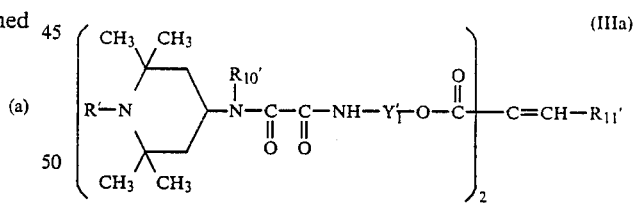
(IIIa)

in which
R' is hydrogen, $C_{1-4}$alkyl, —CO—$R_5'$ or —CO—CH=CH$_2$, where $R_5'$ is $C_{1-4}$alkyl or —CO—O—$C_{1-4}$alkyl;
$R_{10}'$ is hydrogen or methyl;
$Y_1'$ is —(CH$_2$)$_p$—, —CH$_2$CH$_2$—O—CH$_2$CH$_2$—, —C(CH$_3$)$_2$—CH$_2$—, —C(CH$_3$)$_2$— —C(CH$_3$)$_2$—CH$_2$CH(CH$_3$)— or —CH$_2$C(CH$_3$)$_2$—CH$_2$—, where p is 1, 2 or 3; and
$R_{11}'$ is phenyl, unsubstituted or substituted by one or two groups selected from $C_{1-2}$alkyl and $C_{1-2}$alkoxy, or by one —OH group.

Preferred compounds of formula IV are of formula IVa

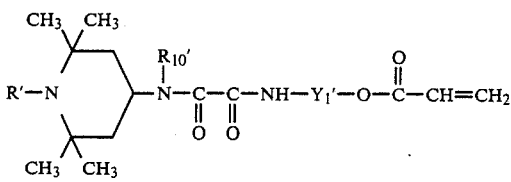

(IVa)

in which
R' is hydrogen, C$_{1-4}$alkyl, —CO—R$_5$' or —CO—CH=CH$_2$ where R$_5$' is C$_{1-4}$alkyl or —CO—O—C$_{1-4}$alkyl;
R$_{10}$' is methyl or hydrogen; and
Y$_1$' is —(CH$_2$)$_p$—, —CH$_2$CH$_2$—O—CH$_2$CH$_2$—, —C(CH$_3$)$_2$—CH$_2$—, —C(CH$_3$)$_2$—, —C(CH$_3$)$_2$—CH$_2$CH(CH$_3$)— or —CH$_2$C(CH$_3$)$_2$—CH$_2$—, where p is 1, 2 or 3.

Preferred compounds of formula V are of formula Va

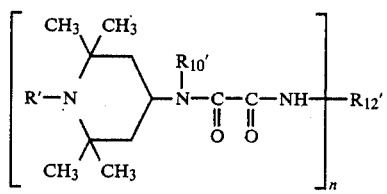

(Va)

in which
n is 1 or 2;
R' is hydrogen, C$_{1-4}$alkyl, —CO—R$_5$' or —CO—CH=CH$_2$, where R$_5$' is C$_{1-4}$alkyl or —CO—O—C$_{1-4}$alkyl;
R$_{10}$' is hydrogen or methyl and
when n=1, R$_{12}$' is linear or branched C$_{8-12}$alkyl or a group of formula a' or b'

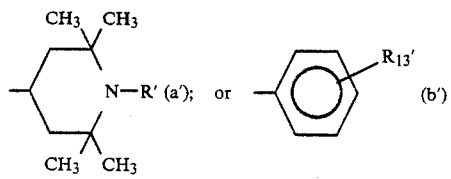

where R$_{13}$' is methoxy, ethoxy or hydrogen;
with the proviso that
(i) when R$_{12}$' is a group of formula a' at least one group R' is other than hydrogen, and
(ii) when R' is hydrogen and R$_{12}$' is a group of formula b' then R$_{13}$' is not hydrogen; and
when n=2, R$_{12}$' is linear or branched C$_{1-8}$alkylene.

Preferred compounds of formula VI are of formula VIa

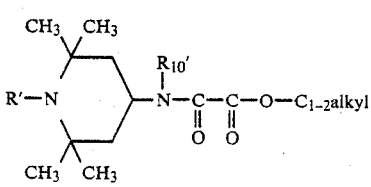

(VIa)

in which
R' is hydrogen, C$_{1-4}$alkyl, —CO—R$_5$' or —CO—CH=CH$_2$, where R$_5$' is C$_{1-4}$alkyl or —CO—O—C$_{1-4}$alkyl; and
R$_{10}$' is hydrogen or methyl.

Compounds of formula I where R$_4$ is an amide forming group can be prepared by reacting a compound of formula VI wherein n=1 and x is 1-4 with a compound of formula VII

(VII)

where R$_{10}$ and R$_{40}$ are as defined above.

Compounds of formula I, where R$_4$ is an ester forming group, can be prepared by reacting a compound of formula VIII

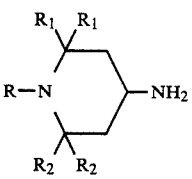

(VIII)

with a compound of the formula (IX)

R$_6$—O—CO—CO—O—R$_{40}$ (IX)

where
R$_6$ is hydrogen or C$_{1-6}$alkyl.

Compounds of formula VII, VIII and IX are known or may be made from known compounds by known methods.

Compounds of formula II can be prepared by reacting a compound of formula VI, wherein n=1 with a compound of formula XI

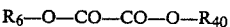

(XI)

at elevated temperatures, preferably from 40° to 180° C., more preferably from 80° to 150° C.

Compounds of formula III can be prepared by reacting 2 n moles of a compound of formula XII

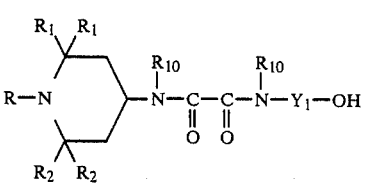

(XII)

with 1 mole of an acid of formula XIII

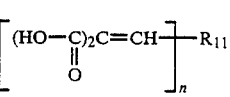

(XIII)

or C$_{1-2}$alkyl ester thereof;
at elevated temperature, preferably from 40° to 200° C., more preferably 80° to 190° C.

Compounds of formula IV can be prepared by reacting a compound of formula XIV

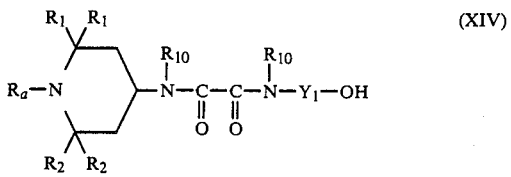

(XIV)

where $R_a$ has a significance of R except —CO—C($R_{10}$)=$CH_2$ with acrylic acid, methacrylic acid or an acid of the formula XV

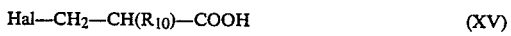

Hal—$CH_2$—CH($R_{10}$)—COOH  (XV)

where Hal is chloro or bromo, or a functional acid derivative (e.g. an $C_{1-2}$alkyl ester) thereof.

The compound of formula XV undergoes cleavage of H-Hal to form the acrylic or methacrylic acid ester.

Preferred functional derivatives of acrylic acid, methacrylic acid or of the compound of formula XV are the acid chloride or the $C_{1-4}$alkyl esters.

Compounds of formula V can be prepared by reacting n mols of a compound of formula VI wherein n=1 with 1 mol of a compound of formula XVI

where the symbols are defined above.

Compounds of formula XIV can be prepared by reacting a compound of formula VI wherein n=1 with a compound of formula XVII

H—N($R_{10}$)—$Y_1$—OH  (XVII)

Further, according to the invention there is provided a composition comprising a polymeric material and a compound of formula I defined above.

Further, according to the invention there is provided a method for stabilising a lacquer composition based on acrylic, alkyd or polyester resins (which, if desired can be crosslinked with melamine/formaldehyde resins, epoxide resins or polyisocyanates) which comprises incorporating into the resin a 4-oxalamido-2,2,6,6-tetraalkylpiperidine compound.

Further, according to the invention there is provided a lacquer composition based on acrylic, alkyd and/or polyester resin (which if desired, can be crosslinked with melamine/formaldehyde resins, epoxide resins or polyisocyanates) containing one or more 4-oxalamido-2,2,6,6-tetraalkylpiperidine compounds.

Preferred 4-oxalamido-2,2,6,6-tetraalkylpiperidine compound are N-unsubstituted, N-alkyl substituted or N-acyl substituted.

More preferred 4-oxalamido-2,2,6,6-tetraalkylpiperidine compounds are those containing one or more groups of formula XXX

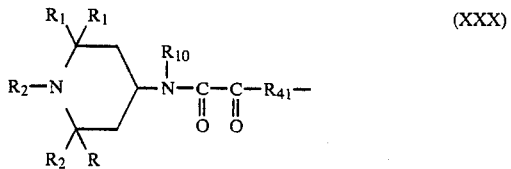

(XXX)

where $R_{41}$ is —N($R_{10}$)— or —O— and where the other symbols are as defined above.

Preferred compounds containing one or more groups of formula XXX are those of formula I (excluding both provisos); more preferred are those of formulae II to V defined above (excluding the provisos of the compounds of formula V).

Most preferred compounds of formula XXX are those of any one of formula IIa to Va (excluding the provisos of the compounds of formula (Va).

Lacquer compositions according to the invention can be metallic one or two layer lacquer compositions or uni one or two layer lacquer compositions. Preferably a lacquer composition according to the invention is a stoving lacquer composition.

Compounds of formula I are useful as stabilizers to protect polymeric materials against degradation by light. The compounds have particularly good solubility and miscibility in solvent systems and in liquid polymers as well as in prepolymers, which makes them useable in a wide range of polymeric materials.

The concentration of compound of formula I employed in the polymeric material is suitably 0.01 to 5% by weight, preferably 0.02% to 1% by weight. The compound may be added before, during or after the polymerization step, and may be added in solid form; in solution, preferably as a liquid concentrate containing from 20 to 80% by weight of compound of formula I; or as a solid masterbatch composition containing 20 to 80% by weight of compound of formula I and 80 to 20% by weight of a solid polymeric material which is identical with or compatible with the polymeric material to be stabilized.

Suitable polymeric metarials include plastic materials for example polyethylene, polypropylene, ethylene/propylene copolymers, polyvinyl chloride, polyester; polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material. The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compounds according to the invention. The compounds may be mixed with monomer, prepolymer or precondensate, and the polymerisation or condensation reaction carried out subsequently. This will of course be the preferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones; indolin-2-ones and sterically hindered phenols such as β-(4-hydroxy-3,5-ditert.-butylphenyl)-propionyl stearate, methane tetrakis(methylene-3(3′,5′-ditert.-butyl-4-hydroxy-phenyl-)-propionate], 1,3,3-tris-(2-methyl-4-hydroxy-5-tert.-butyl phenyl)-butane, 1,3,5-tris(4-tert.-butyl-3-hydroxy-2,6-di-methylbenzyl)-1,3,5-triazin-2,4,6(1H,3H,5H)-trione, bis-(4-tert.-butyl-3-hydroxy-2,6-di-methylbenzyl)dithiolterephthalate, tris(3,5-ditert.-butyl-4-hydroxybenzyl)isocyanurate, the triester of β-(4-hydroxy-3,5-ditert.-butylphenyl)propionic acid with 1,3,4-tris-(2-hydroxyethyl)-5-triazin-2,4,6(1H,3H,5H)-trione, bis[3,3-bis-(4′-hydroxy-3-tert.-butylphenyl)-butyricacid]glycol ester, 1,3,5-trimethyl-2,4,6-tris-(3,5-ditert.-butyl-4-hydroxy-benzyl)benzene, 2,2′-methylene-bis-(4-methyl-6-tert.-butyl-phenyl)-terephthalate, 4,4-methylene-bis-(2,6-ditert.-butyl-phenol), 4,4′-butylidine-bis-(tert.-butylmetacresol), 2,2′-methylene-bis-(4-methyl-6-tert.-butyl-phenol).

Sulphur containing antioxidative co-stabilizers which may be used include for example distearylthiodipropionate, di-laurylthiodipropionate, methane tetrakis(methylene-3-hexylthiopropionate), methane tetrakis(methylene-3-dodecylthiopropionate) and dioctadecyl-disulphide. Phosphorus-containing co-stabilizers include for example trinonylphenyl phosphite, 4,9-distearyl-3,5,8,10-tetraoxadiphosphaspiroundecane, tris-(2,4-ditert.butylphenyl)phosphite and tetrakis(2,3-ditert.-butylphenyl)-4,4′-biphenylene diphosphonite. Further additives such as aminoaryl compounds and U.V.-absorbers and light stabilizers e.g. 2-(2′-hydroxy-phenyl)-benzotriazole, 2-hydroxybenzophenone, 1,3-bis-(2′-hydroxybenzyl)benzene, salicylates, cinnamates, benzoates and substituted benzoates, sterically hindered amines and oxalic acid diamides may be used. Other known types of additives, e.g. flame retardants and antistatic agents, may also be added.

Preferably a compound of formula XX

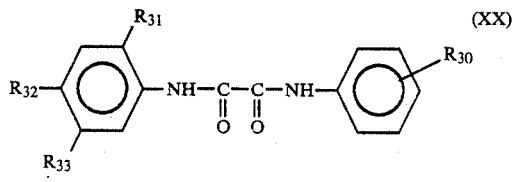

in which $R_{30}$ is $C_{6-22}$alkyl or $C_{6-22}$alkoxy;

$R_{31}$ and $R_{32}$ independently, are selected from hydrogen, $C_{1-8}$alkyl, $C_{1-12}$alkoxy, $C_{1-12}$alkoxy, $C_{1-12}$alkylthio, phenoxy and phenylthio provided that only one of $R_{31}$ and $R_{32}$ is alkylthio, phenoxy or phenylthio; and $R_{33}$ is hydrogen or $C_{1-8}$alkyl; is added to a compound of formula I.

The compounds of the invention can also be used in photopolymeric substrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer-coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automotive finishes are metallic finishes, which contain flakes of metal, usually aluminium, in order to provide optical effects due to reflection. Such finishes are often two-coat finishes, in which a clear top coat finish is applied over a base coat finish containing a single pigment and/or metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyester resin. These polyurethane 2-component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. Such polyacrylate resins are described in U.S. Pat. No. 3,062,753, the contents of which are incorporated herein by reference.

The compounds of formula I are particularly useful in acid catalysed stoving finishes particularly in the top coat of two layer metallic finishes.

The compounds of formula I may be added to the finish at any stage in its manufacture, and may be added in solid form or in solution, preferably in the form of a liquid concentrate in a suitable solvent or in the form of a dispersion in water or organic solvent.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I are to be added to the liquid or powder finishes before stoving or hardening. Preferably the compounds of formula I are used in liquid finishes since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The addition of from 0.01 to 8% by weight, preferably 0.2 to 4% by weight of one or more compounds of formula I gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces. Compounds of formula III and IV can be co-polymerised with suitable monomers (particularly for those used in lacquers) e.g. acrylic based and alkyd based monomers.

The invention will now be illustrated by the following Examples in which all parts are by weight and temperatures are in °C.

EXAMPLE 1

128.1 g of the compound of formula 1b

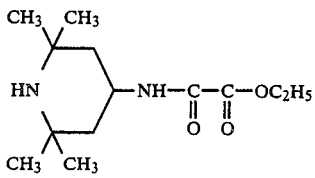

(m.p. 54°–56° C.) are added to 30.5 g of ethanolamine and 2.0 g of boric acid and the mixture is heated to 140°, at which temperature the ethanol dissociates and a thick white mass results. 200 ml of methanol and 50 ml of water are added and a clear colourless solution results. The resulting product precipitates as a white crystals. The product is filtered and dried. 103 g of the product of formula 1a

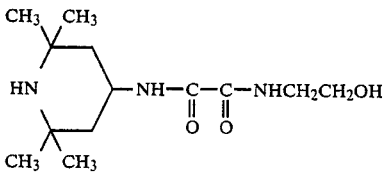

results which is a yield of 76.5% of theory. The melting point of the product is 190°–191° C.

EXAMPLE 2

128.1 g of the compound of formula 1b (defined in Example 1) are added to 100 ml of chloro-benzene, 45.0 g of 2-amino-2-methyl-1-propanol and 1.7 g of tetrabutyl-orthotitanate and this mixture is heated in a bath to 130°. At a temperature in the range 105° to 115° the reacting alcohol dissociates. 100 ml of hexane are added to the mixture and the white resulting precipitate is filtered, washed with water and dried until a constant weight is obtained.

The resulting product is of formula 2a

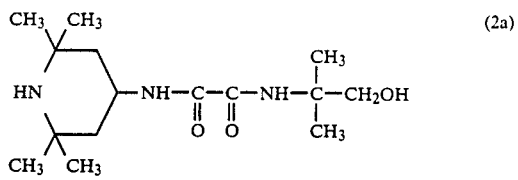

and gives a yield of 82.3% of theory. The melting point is 179°–181°.

EXAMPLES 3 TO 11

Compounds of the formula

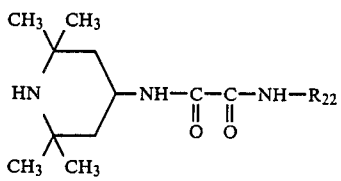

where $R_{22}$ is defined in Table 1 below, can be made from appropriate reactants by a method analogous to Example 1.

TABLE 1

| Example No. | $R_{22}$ | melting point |
|---|---|---|
| 3 | —CH$_2$CH(OH)—CH$_3$ | |
| 4 | —CH$_2$CH$_2$—O—CH$_2$OH | |
| 5 | —CH$_2$CH$_2$NH—CH$_2$CH$_2$OH | |
| 6 | —CH$_2$CH$_2$NH—CH$_2$CH(OH)—CH$_3$ | |
| 7 | —CH$_2$CH$_2$CH$_2$OH | |
| 8 | $\begin{array}{c}\text{CH}_2\text{CH}_3\\|\\-\text{CH}-\text{CH}_2\text{OH}\end{array}$ | |
| 9 | —CH$_2$—C(CH$_3$)$_2$—CH$_2$OH | |
| 10 | —C(CH$_2$OH)$_2$—CH$_2$OH | |
| 11 | —C(CH$_3$)$_2$—CH$_2$—CH(CH$_3$)OH | |

EXAMPLE 12

The compound of formula 12a

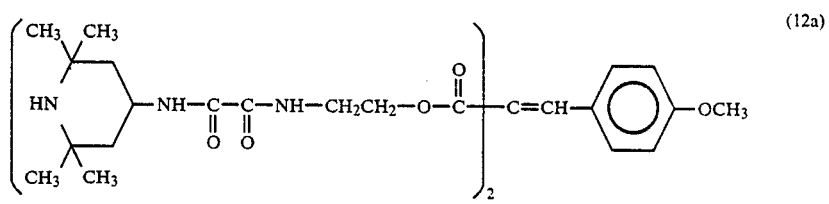

can be prepared as follows.

27.1 g of the compound of formula (1a) (defined in Example 1)

13.9 g of the compound of formula 12b

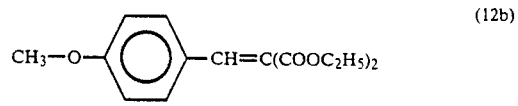

and 0.5 g of tetrabutyl orthotitanate are stirred in a reaction vessel at 170°–190° for 6 hours. The resulting red-brown solution is cooled to 100° and added to 100 ml of ethanol. The solution is treated, while still warm, with silica gel 60 and fullers earth (a bleaching clay), filtered and the solvent is evaporated off. The resulting red-brown oil is twice dissolved in toluene, treated with silica gel 60 and fullers earth, filtered, cooled and added to ether. The product is a light yellow precipitate. This is filtered and dried. The product has a melting point of 184°–188°.

EXAMPLE 13 TO 17

Compounds of the formula

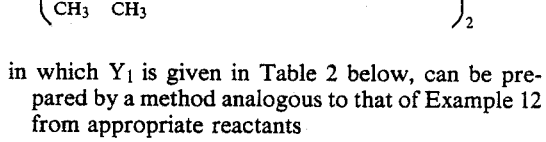

in which $Y_1$ is given in Table 2 below, can be prepared by a method analogous to that of Example 12 from appropriate reactants

TABLE 2

| Examples | $Y_1$ | |
|---|---|---|
| 13 | —CH$_2$CH$_2$—O—CH$_2$CH$_2$— | |
| 14 | —C(CH$_3$)$_2$—CH$_2$— | oil |
| 15 | —C(CH$_3$)$_2$—CH (CH$_3$)— | |
| 16 | —CH$_2$—CH$_2$—CH$_2$— | |
| 17 | —CH$_2$C(CH$_3$)$_2$—CH$_2$— | oil |

EXAMPLE 18

13.6 Parts of the compound of formula 1a (defined in Example 1) are dissolved in 100 parts by volume (based on the volume of 100 parts by weight water), methylenechloride and 30.3 parts of triethylamine are added and cooled to −10°. 12.6 Parts of 3-chloropropionic acid chloride is added slowly (drop by drop), stirred for 6 hours while cooling and stirred a further 12 hours at room temperature. The methylenechloride solution is then washed 3 times with cold water, decanted, the water is then separated off and the solution is then dried, treated with bleaching clay (Tonsil AG), filtered and concentrated at 40°. The residue is then dissolved in acetone, treated with charcoal and bleaching clay, filtered and then reconcentrated. The residue is then contacted with diethylether, filtered under vacuum and dried at room temperature.

The resulting product is of formula 18b

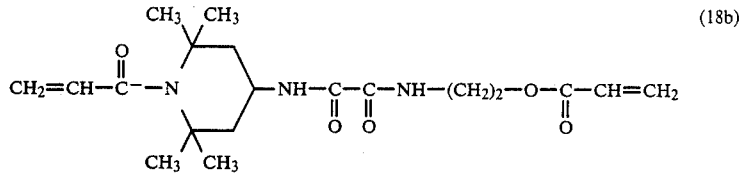

and has a melting point of 132°–134°.

EXAMPLES 19 TO 23

By a method analogous to that of Example 18 compounds of the formula

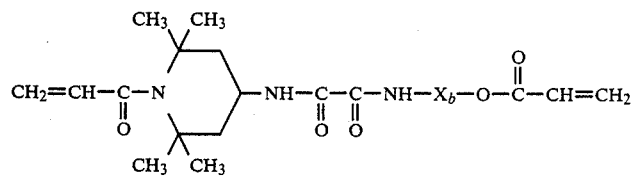

can be obtained in which $X_b$ is defined in Table 3 below.

TABLE 3

| Example | $X_b$ |
|---|---|
| 19 | —CH$_2$CH$_2$—O—CH$_2$CH$_2$— |
| 20 | —C(CH$_3$)$_2$—CH$_2$— |
| 21 | —C(CH$_3$)$_2$—CH$_2$—CH(CH$_3$)— |
| 22 | —CH$_2$—CH$_2$CH$_2$ |
| 23 | —CH$_2$C(CH$_3$)2—CH$_2$— |

EXAMPLE 24

(a) Preparation of the compound of formula 1b of Example 1

21.93 Parts of diethyl oxalate are slowly reacted with 7.81 parts of triacetone diamine at room temperature under a nitrogen atmosphere. The temperature rises to about 50°. The mixture is then over 12 hours heated first to 120° then to 135° whilst stirring and then the resulting alcohol is distilled off. The excess diethyl oxalate is then distilled off at 150° under vacuum and the residue is cooled to about 60°, then is added to 500 parts by volume toluene and then 1500 parts by volume hexane. The mixture is then stirred a further 15 minutes and at 40° the residue is filtered off.

In order to purify the residue, it is dissolved in 280 parts by volume toluene and, whilst stirring added to 2800 parts by volume hexane. The light yellow-beige precipitate is then filtered at 10°, dried at 40° and then milled into a powder (m.p. 54°–56°).

(b) Preparation of the compound of formula 24b

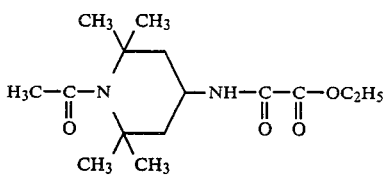

35.9 Parts of the compound of formula 1b are mixed with 84 parts of acetic anhydride for 10 hours at 90°. The excess of acetic anhydride is then distilled off and the residue is dissolved in 1000 parts of toluene (warmed) and the resulting solution is then washed twice with water. The organic phase is then washed with bleaching clay and Kieselgel 60 after which it is filtered. After filtration, the solution is concentrated at 90° under a light vacuum. The residue is dissolved in 280 parts of toluene and then the mixture is stirred in 2800 parts of hexane. The resulting precipitate is filtered after cooling to 10° and stirring for 1 hour. The product is dried and pulverised (m.p. 88°–89°).

(c) Preparation of the compound of formula 24c

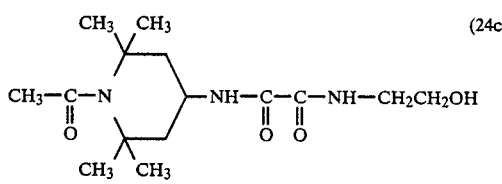

29.8 Parts of the compound of formula 22b, 25 parts by volume of chlorobenzene and 6.1 parts of ethanolamine are stirred together under a weak stream of nitrogen. The temperature rises to about 45°. 0.2 parts of tetrabutylorthotitanate are then added and the reaction mixture is heated to 95°–120° whilst stirring for 4 hours, whereby the resulting ethanol is distilled off. The mixture is then cooled to about 50° and then the mixture is added to 50 parts of methanol whilst stirring after which the mixture is cooled to 0°, filtered and the residue is washed with methanol, water and then methanol once again. The residue is then dried at 80°. The resulting compound of formula 22c has a melting point of 190°–191°.

EXAMPLE 25 TO 36

By a method analogous to that of Example 24 from appropriate reactants, compounds of the formula

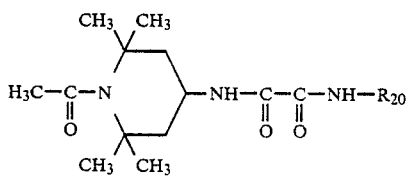

where $R_{20}$ is defined in Table 4 below can be prepared.

TABLE 4

| Example No. | $R_{20}$ | melting point |
|---|---|---|
| 25 | ![structure with N-C(=O)-CH3 on tetramethylpiperidine] | 252–255° |
| 26 | —nC$_8$H$_{17}$ | 134–135° |
| 27 | —C(CH$_3$)$_2$—CH$_2$OH | 73–74° |
| 28 | —CH(CH$_2$CH$_3$)—CH$_2$OH | 180–181° |
| 29 | —CH$_2$CH$_2$CH$_2$OH | 190–191° |
| 30 | —CH$_2$(CH$_3$)$_2$—CH$_2$OH | 136–137° |
| 31 | —CH$_2$CH$_2$—O—CH$_2$CH$_2$OH | 135–136° |
| 32 | —n-C$_{12}$H$_{25}$ | 104–105° |
| 33 | —n-C$_{18}$H$_{37}$ | 97–98° |
| 34 | —OC$_2$H$_5$-phenyl | ~103° |
| 35 | —CH$_2$CH(OH)CH$_3$ | 179–180° |
| 36 | —(CH$_2$)$_8$—NH—C(O)—C(O)—NH—[tetramethylpiperidine-N—C(O)—CH$_3$] | 176–178° |

APPLICATION EXAMPLE A

A clear finish of
80 Parts of Viacryl SC 344 (a 50% solution of an acryl resin from Vianova),
13.9 Parts of Maprenal MF 80 (a 72% solution of a melamine resin from Hoechst) and
4.1 Parts of Byketol OK (from Byk-Malinckrodt)
is added to 2 parts of a compound of formula 1a (described in Example 1). After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 um. The resulting coating is then hardened at 140° for 30 minutes. The coating shows very good resistance to U.V. light and weathering.

APPLICATION EXAMPLE B

A clear finish of
29.5 Parts of Setalux C-1502 XX-60 (a 60% solution of an acryl resin from Synthese B.V.),
39.2 Parts of Setalux C-1382 BX-45 (a 45% solution of an acryl resin from Synthese B.V.),
21.4 Parts of Setamine US-138 BB-70 (a 70% solution of a melamine resin from Synthese B.V.),
2.5 Parts of Baysilonoil [(2% solution in Xylene) from Bayer] and
7.4 Parts of Depanol Y (a solvent from Hoechst)
is stirred together with 2.5 parts of a compound of formula 1a (described in Example 1) and 2 parts of an acid catalyst derived from phosphoric acid (Type: Catalyst 269-9 from American Cyanamid) to form a homogeneous mixture. The finish is applied conventionally (according to known 2 layer procedure) to a metallic or single pigment finish whilst both are still wet by spraying to form a layer having a thickness of 30 to 40 um. The resulting coating is then hardened at 110° for 20 minutes. The coating shows very good resistance to U.V. light and weathering.

APPLICATION EXAMPLE C

A clear finish of
75 Parts Macrynal SH 510N (a hydroxy containing acryl resin from Bayer)
2 Parts of Baysilon-oil A [(1% solution in xylene) from Bayer]
0.3 Parts of dibutyl zinc dilaurate
0.35 Parts diethanolamine
5.0 Parts of ethylglycol acetate
5.0 Parts of Solveso 100
6.0 Parts of Xylene and
6.36 Parts of butyl acetate
is added to 2.5 parts of a compound of formula Ia (described in Example 1) and 30 parts of Desmodur N 75 (from Bayer). The homogeneous mixture so formed is applied conventionally (according to the known 2 layer procedure) to a metallic or single pigment finish whilst both are still wet by spraying to form a layer having a thickness of 30 to 40 um and the resulting coating is hardened over 20 minutes at 80° to 90°. The resulting 2K-PUR coating shows a good resistance to U.V. light and weathering.

APPLICATION EXAMPLE D

A single white pigmented finish of
14.30 Parts of Setamine US-132 BB70 (a 70% solution of a melamine resin from Synthese)
57.15 Parts of Setal 84 W-70 (a 70% solution of an alkyd resin from Synthese)
7.70 Parts of n-butanol
1.85 Parts of butylglycol acetate
9.50 parts of Xylene and
25 Parts of titanium dioxide (Rutil type)
is added with 1.38 parts of the product of formula Ia (see Example 1). The finish is conventionally applied to a grounded steel metal to which a filler of layer thickness 20 to 30 um has been annealed, by spraying and after standing for 30 minutes at room temperature the steel metal surface is annealed at 120° C. for 30 minutes. The resulting coating shows very good resistance to U.V. light and weathering.

In Application Examples A to D instead of the product of formula Ia, an appropriate amount of the product of any one of the other Examples 2 to 36 can be used.

I claim:

1. A method of stabilizing a lacquer composition based on a member selected from the group consisting of acrylic resins, alkyd resins, polyester resins and acrylic resins, alkyd resins and polyester resins crosslinked with melamine/formaldehyde resins, epoxide resins or polyisocyanates, which comprises incorporating into the resin a light-stabilizing-effective amount of at least one 4-oxalamido-2,2,6,6-tetraalkylpiperidine compound of formula I

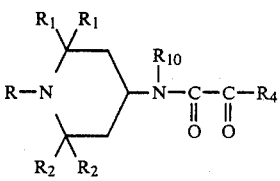

in which
R is hydrogen, oxygen, $C_{1-8}$alkyl or $-CO-R_5$; each $R_1$, independently, is $-CH_3$ or $-CH_2(C_{1-4}alkyl)$ or both groups $R_1$ form a group $-CH_2)_5$; each $R_2$, independently, is $-CH_3$ or $-CH_2(C_{1-4}alkyl)$ or both groups $R_2$ form a group $-CH_2)_5$;
$R_4$ is an amide-forming group;
$R_5$ is $-C(R_{10})=CH_2$, $C_{1-6}$alkyl, phenyl, $-CO-O-C_{1-4}$alkyl or $-NR_7R_8$;
$R_7$ is hydrogen, $C_{1-12}$alkyl, $C_{5-6}$ cycloalkyl, phenyl, phenyl $C_{1-4}$alkyl or $C_{1-12}$alkylphenyl;
$R_8$ is $C_{1-12}$alkyl or hydrogen; and
$R_{10}$ is hydrogen or $C_{1-4}$alkyl.

2. A lacquer composition based on a member selected from the group consistency of acrylic resins, alkyd resins, polyester resins and acrylic resins, alkyd resins and polyester resins crosslinked with melamine/formaldehyde resins, epoxide resins or polyisocyanates, which contains at least one 4-oxalamido-2,2,6,6-tetraalkylpiperidine compound of formula I

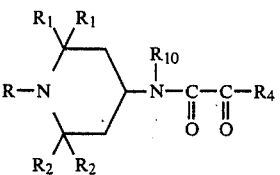

in which
R is hydrogen, oxygen, $C_{1-8}$alkyl or $-CO-R_5$; each $R_1$, independently, is $-CH_3$ or $-CH_2(C_{1-4}alkyl)$ or both groups $R_1$ form a group $-CH_2)_5$;
each $R_2$, independently, is $-CH_3$ or $-CH_2(C_{1-4}alkyl)$ or both groups $R_2$ form a group $-CH_2)_5$;
$R_4$ is an amide-forming group;
$R_5$ is $-C(R_{10})=CH_2$, $C_{1-6}$alkyl, phenyl, $-CO-O-C_{1-4}$alkyl or $-NR_7R_8$;
$R_7$ is hydrogen, $C_{1-12}$alkyl, $C_{5-6}$cycloalkyl, phenyl, phenyl $C_{1-4}$alkyl or $C_{1-12}$alkylphenyl;
$R_8$ is $C_{1-12}$alkyl or hydrogen; and
$R_{10}$ is hydrogen or $C_{1-4}$alkyl.

3. A method according to claim 1 wherein the compound of formula I is added in an amount of 0.01 to 8% by weight.

4. A method according to claim 1 wherein the 4-oxalamido-2,2,6,6-tetraalkylpiperidine compound is added in an amount of 0.01 to 8% by weight.

5. A composition according to claim 2 wherein the compound of formula I is present in an amount of 0.01 to 8% by weight.

6. A composition according to claim 1 wherein the 4-oxalamido-2,2,6,6-tetraalkylpiperidine compound is present in an amount of 0.01 to 8% by weight.

7. A composition according to claim 1 wherein the 4-oxalamido-2,2,6,6-tetraalkylpiperidine compound is a compound of formula II.

8. A composition according to claim 1 wherein the 4-oxalamido-2,2,6,6-tetraalkylpiperidine compound is a compound of formula III.

9. A composition according to claim 1 wherein the 4-oxalamido-2,2,6,6-tetraalkylpiperidine compound is a compound of formula IV.

10. A composition according to claim 1 wherein the 4-oxalamido-2,2,6,6-tetraalkylpiperidine compound is a compound of formula V.

11. A composition according to claim 6 wherein the 4-oxalamido-2,2,6,6-tetraalkylpiperidine compound is a compound of formula IIa

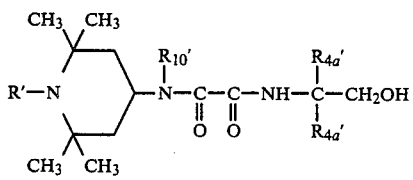

in which
R' is hydrogen, $C_{1-4}$alkyl, —CO—$R_5$' or —CO—CH=CH$_2$
where
$R_5$' is $C_{1-4}$alkyl or —CO—O—$C_{1-4}$alkyl;
each $R_{4a}$' independently, is hydrogen or methyl and
$R_{10}$' is hydrogen or methyl.

12. A composition according to claim 6 wherein the 4-oxalamido-2,2,6,6-tetraalkylpiperidine compound is a compound of formula IIIa

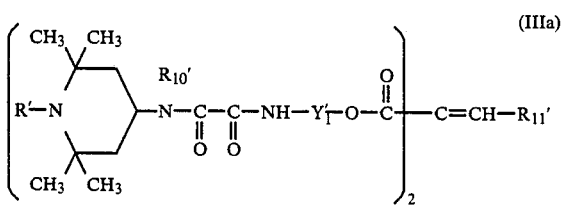

in which R' is hydrogen, $C_{1-4}$alkyl, —CO—$R_5$' or —CO—CH=CH$_2$,
wherein
$R_5$' is $C_{1-4}$alkyl or —CO—O—$C_{1-4}$alkyl;
$R_{10}$' is hydrogen or methyl;
$Y_1$' is —(CH$_2$)$_p$—, —CH$_2$CH$_2$—O—CH$_2$CH$_2$—, —C(CH$_3$)$_2$—CH$_2$—; —C(CH$_3$)$_2$—; —C(CH$_3$)$_2$—CH$_2$CH(CH$_3$)— or —CH$_2$C(CH$_3$)$_2$—CH$_2$—;
where p is 1, 2, or 3; and
$R_{11}$' is phenyl, unsubstituted or substituted by one or two groups selected from $C_{1-2}$alkyl and $C_{1-2}$alkoxy, or by one —OH group.

13. A composition according to claim 6 wherein the 4-oxalamido-2,2,6,6-tetraalkylpiperidine compound is a compound of formula IVa

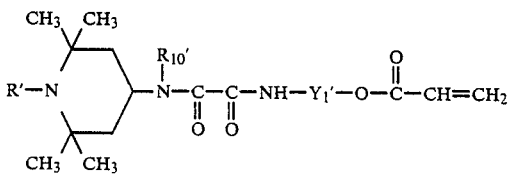

in which R' is hydrogen, $C_{1-4}$alkyl, —CO—$R_5$' or —CO—CH=CH$_2$,
where $R_5$' is $C_{1-4}$alkyl or —CO—O—$C_{1-4}$alkyl;
$R_{10}$' is hydrogen or methyl;
$Y_1$' is —(CH$_2$)$_p$—, —CH$_2$CH$_2$—O—CH$_2$CH$_2$—; —C(CH$_3$)$_2$—CH$_2$—; —C(CH$_3$)$_2$—; —C(CH$_3$)$_2$—CH$_2$CH(CH$_3$)— or —CH$_2$C(CH$_3$)$_2$—CH$_2$—;
where p is 1, 2, or 3.

14. A composition according to claim 6 wherein the 4-oxalamido-2,2,6,6-tetraalkylpiperidine compound is a compound of formula Va

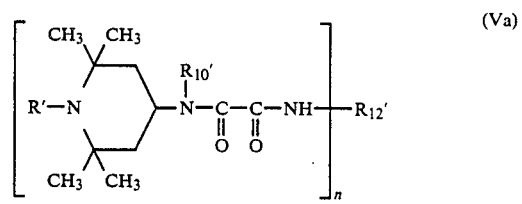

in which n is 1 or 2;
R' is hydrogen, $C_{1-4}$alkyl, —CO—$R_5$' or —CO—CH=CH$_2$, where $R_5$' is $C_{1-4}$alkyl or —CO—O—$C_{1-4}$alkyl;
$R_{10}$' is hydrogen or methyl and
when n is 1, $R_{12}$' is linear or branched $C_{8-12}$alkyl or a group of formula a' or b'

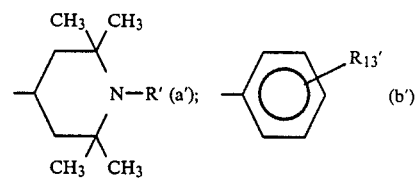

where $R_{13}$' is methoxy, ethoxy or hydrogen; with the proviso that
when $R_{12}$' is a group of formula a' at least one group R' is other than hydrogen, and
when R' is hydrogen and $R_{12}$' is a group of formula b' then $R_{13}$' is not hydrogen; and
when n is 2, $R_{12}$' is linear or branched $C_{1-8}$alkylene.

15. A method according to claim 1, in which the 4-oxalamido-2,2,6,6-tetraalkylpiperidine compound is of any one of formulae II to V

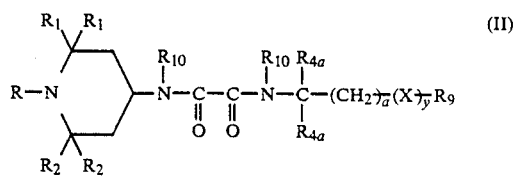

in which
X is —O—, —NH— or —S—;
y is 0 or 1;
a is 0 or 1;
each $R_{4a}$, independently, is hydrogen, CH$_2$OH or $C_{1-4}$alkyl;
and $R_9$ is linear or branched $C_{1-6}$alkyl unsubstituted or mono- or di-substituted by OH;

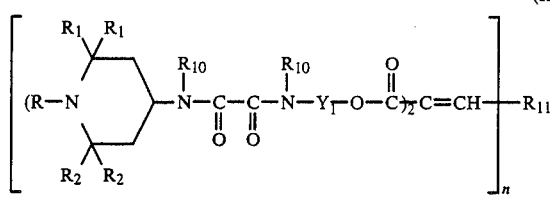

in which
n is 1 or 2;
$Y_1$ is linear or branched unsubstituted $C_{1-8}$alkylene, uninterrupted or interrupted by 1 or 2 groups selected from —O— and —NH—;
and $R_{11}$ is an aromatic group unsubstituted or substituted by one or two groups selected from $C_{1-4}$alkyl, $C_{1-4}$alkoxy, and not more than one —OH;

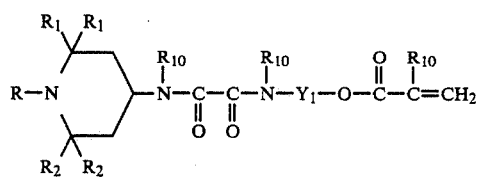

in which $Y_1$ is as defined above;

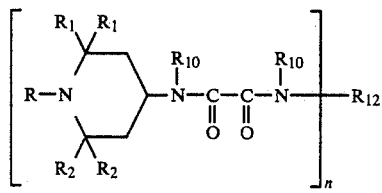

in which R, $R_1$, $R_2$ and $R_{10}$ are as defined in claim 3;
$R_{12}$, when n is 1, is linear or branched unsubstituted $C_{8-22}$alkyl or a group of formula (a) or (b)

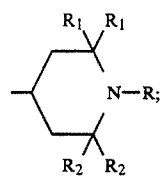

or

where
$R_{13}$ is $C_{1-4}$alkyl or $C_{1-4}$alkoxy, or hydrogen;
$R_{12}$, when n is 2, is linear or branched $C_{1-12}$alkylene or $C_{2-12}$alkenylene.

16. A composition according to claim 2, in which the 4-oxalamido-2,2,6,6-tetraalkylpipiperidine compound is of any one of formulae II to V

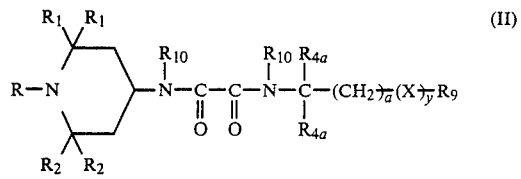

in which
X is —O—, —NH— or —S—;
y is 0 or 1;
a is 0 or 1;
each $R_{4a}$, independently, is hydrogen, $CH_2OH$ or $C_{1-4}$alkyl;
and $R_9$ is linear or branched $C_{1-6}$alkyl unsubstituted or mono-or di-substituted by OH;

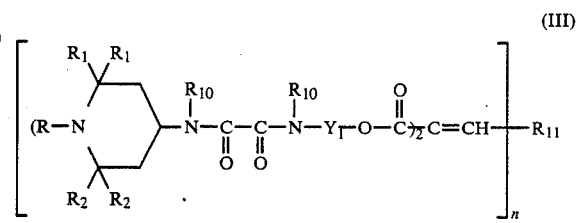

in which
n is 1 or 2;
$Y_1$ is linear or branched unsubstituted $C_{1-8}$alkylene, uninterrupted or interrupted by 1 or 2 groups selected from —O— and —NH—;
and $R_{11}$ is an aromatic group unsubstituted or substituted by one or two groups selected from $C_{1-4}$alkyl, $C_{1-4}$alkoxy, and not more than one —OH;

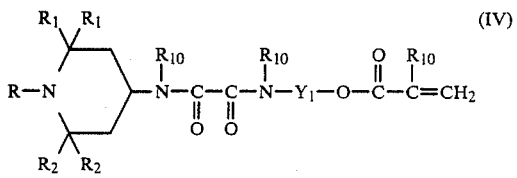

in which $Y_1$ is as defined above;

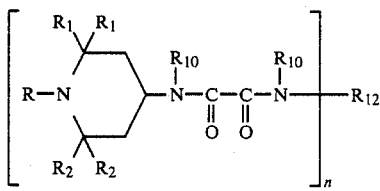

in which
n is 1 or 2,
$R_{12}$, when n is 1, is linear or branched unsubstituted $C_{8-22}$alkyl or a group of formula (a) or (b)

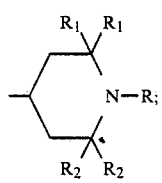

-continued or

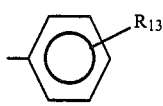

where
R$_{13}$ is C$_{1-4}$alkyl or C$_{1-4}$alkoxy, or hydrogen;
R$_{12}$, when n is 2 (n=2), is linear or branched C$_{1-12}$alkylene or C$_{2-12}$alkenylene.

17. A compound of formula I

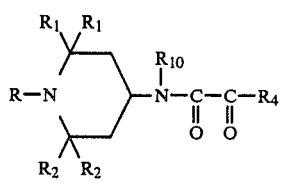

in which R is hydrogen, oxygen, C$_{1-8}$alkyl or —CO—R$_5$, where R$_5$ is —C(R$_{10}$)=CH$_2$, C$_{1-6}$alkyl, phenyl —CO—O—C$_{1-4}$alkyl or —NR$_7$R$_8$ and where R$_7$ is hydrogen, C$_{1-12}$alkyl, C$_{5-6}$cycloalkyl, phenyl, phenyl C$_{1-4}$alkyl or C$_{1-12}$alkylphenyl and R$_8$ is C$_{1-12}$alkyl or hydrogen;

each R$_1$, independently, is —CH$_3$ or —CH$_2$(C$_{1-4}$alkyl) or both groups R$_1$ form a group —(CH$_2$)$_5$—;
each R$_2$, independently, is —CH$_3$ or —CH$_2$(C$_{1-4}$alkyl) or both groups R$_2$ form a group —(CH$_2$)$_5$—;
R$_{10}$ is hydrogen or C$_{1-4}$alkyl; and
R$_4$ is an amide-forming group
with the proviso that when R is hydrogen, then R$_4$ is not
 (i) N unsubstituted 2,2,6,6-tetraalkylpiperidine 4-amino; or
 (ii) unsubstituted phenylamino.

18. A compound according to claim 17 of any one of formula II to V defined below

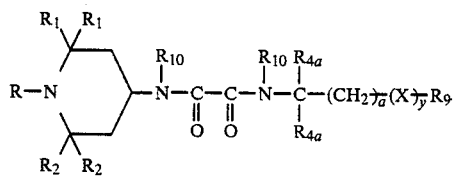

in which
X is —O—, —NH— or —S—;
y is 0 or 1;
a is 0 or 1;
each R$_{4a}$, independently, is hydrogen, CH$_2$OH or C$_{1-4}$alkyl;
and R$_9$ is linear or branched C$_{1-6}$alkyl unsubstituted or mono- or di-substituted by OH;

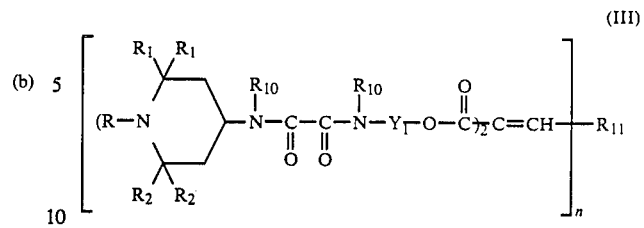

in which
n is 1 or 2;
Y$_1$ is linear or branched unsubstituted C$_{1-8}$alkylene, uninterrupted or interrupted by 1 or 2 groups selected from —O— and —NH—;
and R$_{11}$ is an aromatic group unsubstituted or substituted by one or two groups selected from C$_{1-4}$alkyl, C$_{1-4}$alkoxy, and not more than one —OH;

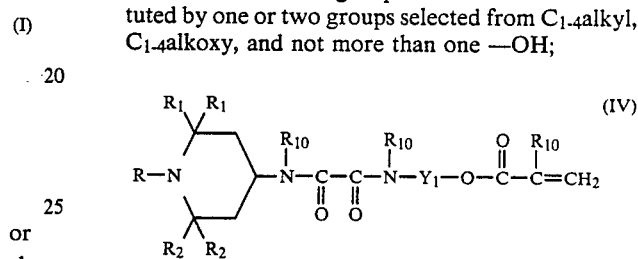

in which Y$_1$ is as defined above;

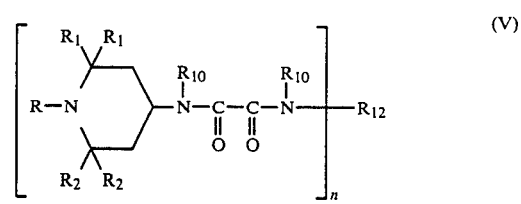

in which
n is 1 or 2;
R$_{12}$, when monovalent (n=1), is linear or branched unsubstituted C$_{8-22}$alkyl or a group of formula (a) or (b)

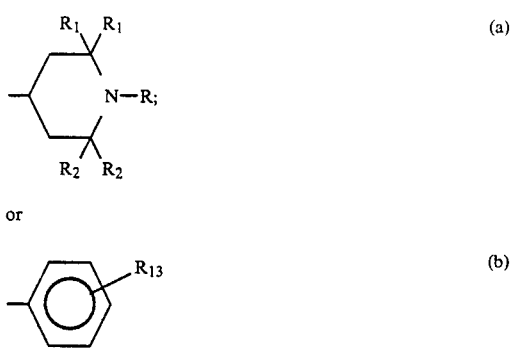

where
R$_{13}$ is C$_{1-4}$alkyl or C$_{1-4}$alkoxy, or halogen;
with the proviso that,
when R$_{12}$ is a group a, at least one group R is other than hydrogen and
when R is hydrogen and R$_{12}$ is a group of formula (b), R$_{13}$ is not hydrogen;
R$_{12}$, when divalent (n=2), is linear or branched C$_{1-12}$alkylene or C$_{2-12}$alkenylene.

19. A compound according to claim 17 of formula IIa

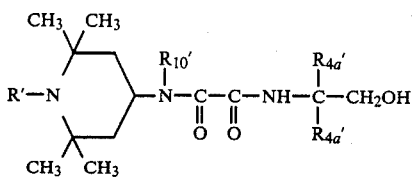

in which R' is hydrogen, $C_{1-4}$alkyl, —CO—$R_5'$ or —CO—CH=CH$_2$ where $R_5'$ is $C_{1-4}$alkyl or —CO—O—$C_{1-4}$alkyl;
each $R_{4a}'$ independently, is hydrogen or methyl and $R_{10}$ is hydrogen or methyl.

20. A compound according to claim 17 of formula IIIa

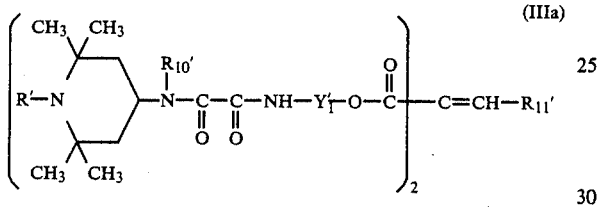

in which R' is hydrogen, $C_{1-4}$alkyl, —CO—$R_5'$ or —CO—CH=CH$_2$ where $R_5'$ is $C_{1-4}$alkyl or —CO—O—$C_{1-4}$alkyl;
$R_{10}'$ is hydrogen or methyl;
$Y_1'$ is —(CH$_2$)$_p$—, —CH$_2$CH$_2$—O—CH$_2$CH$_2$—, —C(CH$_3$)$_2$—CH$_2$—; —C(CH$_3$)$_2$—; —C(CH$_3$)$_2$—CH$_2$CH(CH$_3$)— or —CH$_2$C(CH$_3$)$_2$—CH$_2$—, where p is 1, 2 or 3; and
$R_{11}'$ is phenyl, unsubstituted or substituted by one or two groups selected from $C_{1-2}$alkyl and $C_{1-2}$alkoxy, or by one —OH group.

21. A compound according to claim 17 of formula IVa

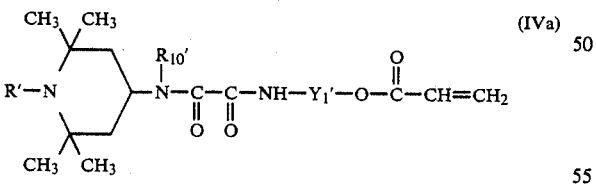

in which R' is hydrogen, $C_{1-4}$alkyl, —CO—$R_5'$ or —CO—CH=CH$_2$ where $R_5'$ is $C_{1-4}$alkyl or —CO—O—$C_{1-4}$alkyl;
$R_{10}'$ is methyl or hydrogen; and
$Y_1'$ is —(CH$_2$)$_p$—; —CH$_2$CH$_2$—O—CH$_2$CH$_2$—, —C(CH$_3$)$_2$—CH$_2$—; —C(CH$_3$)$_2$—; —C(CH$_3$)$_2$—CH$_2$CH(CH$_3$)— or —CH$_2$C(CH$_3$)$_2$—CH$_2$— where p is 1, 2 or 3.

22. A compound according to claim 17 of formula Va

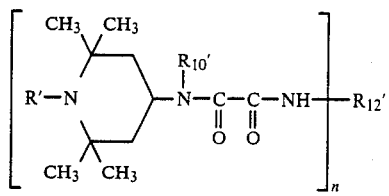

in which n is 1 or 2;
R' is hydrogen, $C_{1-4}$alkyl, —CO—$R_5'$ or —CO—CH=CH$_2$, where $R_5'$ is $C_{1-4}$alkyl or —CO—O—$C_{1-4}$alkyl;
$R_{10}'$ is hydrogen or methyl and
when n=1, $R_{12}'$ is linear or branched $C_{8-12}$alkyl or a group of formula a' or b'

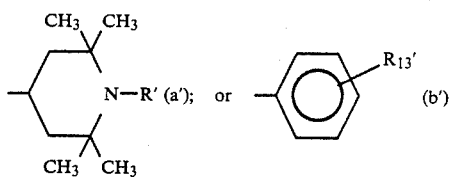

where $R_{13}'$ is methoxy, ethoxy or hydrogen;
with the proviso that
when $R_{12}'$ is a group of formula a' at least one group R' is other than hydrogen, and
when R' is hydrogen and $R_{12}'$ is a group of formula b' then $R_{13}'$ is not hydrogen; and
when n=2, $R_{12}'$ is linear or branched $C_{1-8}$alkylene.

23. A compound according to claim 9 wherein $R_4$ is a group of the formula

wherein $R_{10}$ is hydrogen or $C_{1-4}$alkyl
and $R_{40}$ is unsubstituted or substituted $C_{1-12}$alkyl uninterrupted or interrupted by 1 or 2 groups selected from —O— and —NH—; unsubstituted or substituted $C_{5-6}$cycloalkyl; N-unsubstituted or N-alkyl or N-acyl substituted 2,2,6,6-tetraalkylpiperidine; or unsubstituted or substituted phenyl; and any substituted $C_{5-6}$cycloalkyl or phenyl is substituted by 1 to 3 substituents selected from $C_{1-4}$alkoxy, halogen, $C_{1-6}$alkyl or —OH, provided that only one substituent may be —OH; and any substituent on substituted alkyl is selected from —X)$_y$R$_9$, —OH,

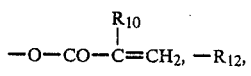

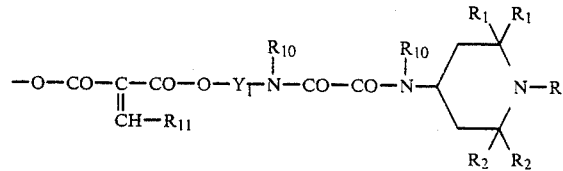

and

-continued

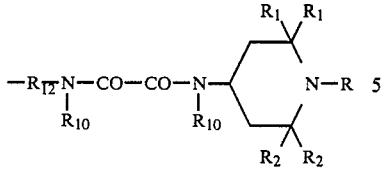

wherein
X is —O—, —NH— or —S—,
$R_9$ is $C_{1-6}$alkyl unsubstituted or mono- or disubstituted by —OH,
$R_{11}$ is a phenyl group unsubstituted or substituted by one or two groups selected from $C_{1-4}$alkyl, $C_{1-4}$alkoxy and not more than one —OH,
$R_{12}$, when monovalent, is linear or branched $C_{8-22}$alkyl or a group of formula (a) or (b)

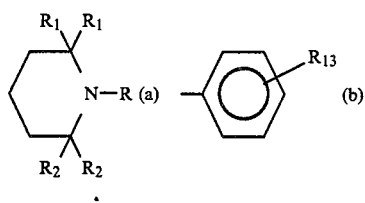

where
$R_{13}$ is $C_{1-4}$alkyl or $C_{1-4}$alkoxy, or hydrogen,
$R_{12}$, when divalent, is linear or branched $C_{1-12}$alkylene or $C_{2-12}$alkenylene;
$Y_1$ is linear or branched unsubstituted $C_{1-8}$alkylene, uninterrupted or interrupted by one or two groups selected from —O— and —NH—;
and y is 0 or 1.

24. A compound according to claim 17 of the formula

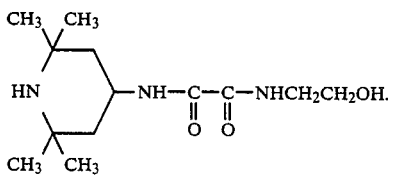

25. A polymeric material selected from the group consisting of polyethylene, polypropylene, ethylene/propylene copolymers, polyvinyl chloride, polyester, polyamide, polyurethane, polyacrylonitrile, ABS, acrylate-styrene-acrylonitrile terpolymers, styrene/acrylonitrile, styrene/butadiene, polybutylene, polystyrene, chlorinated polyethylene, polycarbonate, polymethylmethacrylate, polyphenylene oxide, polypropylene oxide, polyacetals, phenol/formaldehye resins, epoxy resins and natural rubber, which polymeric material contains a light stabilizing-effective amount of a compound according to claim 23.

26. A method according to claim 1 wherein, in the compound of formula I, $R_4$ is a group of the formula

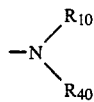

wherein $R_{10}$ is hydrogen or $C_{1-4}$alkyl
and $R_{40}$ is unsubstituted or substituted $C_{1-12}$alkyl uninterrupted or interrupted by 1 or 2 groups selected from —O— and —NH—; unsubstituted or substituted $C_{5-6}$cycloalkyl; N-unsubstituted or N-alkyl or N-acyl substituted 2,2,6,6-tetraalkylpiperidine; or unsubstituted or substituted phenyl; and any substituted $C_{5-6}$ cycloalkyl or phenyl is substituted by 1 to 3 substitutents selected from $C_{1-4}$alkoxy, halogen, $C_{1-6}$alkyl or —OH, provided that only one substituent may be —OH; and any substituent on substituted alkyl is selected from $+X)_yR_9$, —OH,

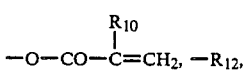

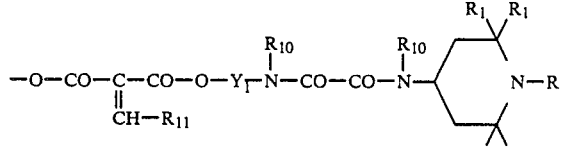

and

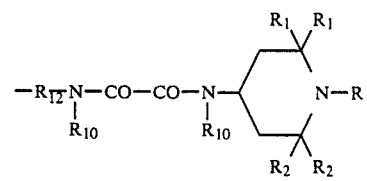

wherein
X is —O—, —NH— or —S—,
$R_9$ is $C_{1-6}$alkyl unsubstituted or mono- or disubstituted by —OH,
$R_{11}$ is a phenyl group unsubstituted or substituted by one or two groups selected from $C_{1-4}$alkyl, $C_{1-4}$alkoxy and not more than one —OH,
$R_{12}$, when monovalent, is linear or branched $C_{8-22}$alkyl or a group of formula (a) or (b)

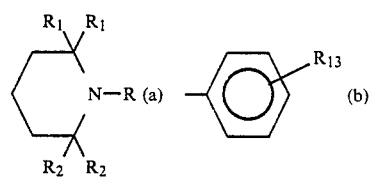

where
$R_{13}$ is $C_{1-4}$alkyl or $C_{1-4}$alkoxy, or hydrogen,
$R_{12}$, when divalent, is linear or branched $C_{1-12}$alkylene or $C_{2-12}$alkenylene;
$Y_1$ is linear or branched unsubstituted $C_{1-8}$alkylene, uninterrupted or interrupted by one or two groups selected from —O— and —NH—;
and y is 0 or 1.

27. A lacquer composition according to claim 2 wherein, in the compound of formula I, $R_4$ is a group of the formula

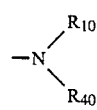

wherein $R_{10}$ is hydrogen or $C_{1-4}$alkyl and $R_{40}$ is unsubstituted or substituted $C_{1-12}$alkyl uninterrupted or interrupted by 1 or 2 groups selected from —O— and —NH—; unsubstituted or substituted $C_{5-6}$cycloalkyl; N-unsubstituted or N-alkyl or N-acyl substituted 2,2,6,6-tetraalkylpiperidine; or unsubstituted or substituted phenyl; and any substituted $C_{5-6}$cycloalkyl or phenyl is substituted by 1 to 3 substituents selected from $C_{1-4}$alkoxy, halogen, $C_{1-6}$alkyl or —OH, provided that only one substituent may be —OH; and any substituent on substituted alkyl is selected from $-(X)_y R_9$, —OH,

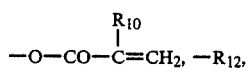

and

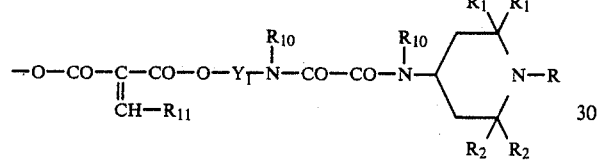

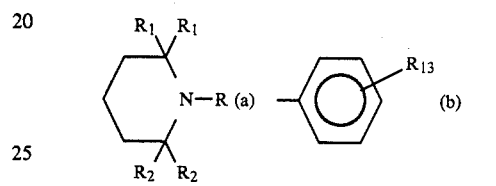

wherein

X is —O—, —NH— or —S—, $R_9$ is $C_{1-6}$alkyl unsubstituted or mono- or disubstituted by —OH, $R_{11}$ is a phenyl group unsubstituted or substituted by one or two groups selected from $C_{1-4}$alkyl, $C_{1-4}$alkoxy and not more than one —OH, $R_{12}$, when monovalent, is linear or branched $C_{8-22}$alkyl or a group of formula (a) or (b)

where $R_{13}$ is $C_{1-4}$alkyl or $C_{1-4}$alkoxy, or hydrogen, $R_{12}$, when divalent, is linear or branched $C_{1-12}$alkylene or $C_{2-12}$alkenylene;

$Y_1$ is linear or branched unsubstituted $C_{1-8}$alkylene, uninterrupted or interrupted by one or two groups selected from —O— and —NH—;

and y is 0 or 1.

* * * * *